United States Patent [19]

Covington et al.

[11] Patent Number: 5,073,340
[45] Date of Patent: Dec. 17, 1991

[54] DEPOSITING A BINDER ON A SOLID SUPPORT

[75] Inventors: Gloria J. Covington, Arnold; Timothy G. Bloomster, Reistertown, both of Md.

[73] Assignee: Becton, Dickinson and Company, Franklin Lakes, N.J.

[21] Appl. No.: 549,670

[22] Filed: Jul. 6, 1990

Related U.S. Application Data

[63] Continuation of Ser. No. 106,075, Oct. 8, 1987, abandoned.

[51] Int. Cl.⁵ .............................................. G01N 31/22
[52] U.S. Cl. .................................... 422/56; 422/57; 422/58; 427/2; 436/169
[58] Field of Search ................................ 422/56-58; 436/169; 435/7, 805; 427/2

[56] References Cited

U.S. PATENT DOCUMENTS

| | | | |
|---|---|---|---|
| 1,967,557 | 7/1934 | John | 422/56 |
| 3,311,024 | 3/1967 | Edenbaum | 422/56 X |
| 4,256,693 | 3/1981 | Kondo et al. | 422/57 X |
| 4,361,648 | 11/1982 | Shuenn-tzong | 435/805 X |
| 4,442,204 | 4/1984 | Greenquist et al. | 435/805 X |
| 4,675,160 | 6/1987 | Talmage et al. | 436/66 X |

Primary Examiner—Jill Johnston
Attorney, Agent, or Firm—Mary M. Allen; Nanette S. Thomas

[57] ABSTRACT

A test device for use in determining analyte wherein binder is supported on a solid support in admixture with a marker whereby the presence and location of binder on the support can be determined prior to the assay. A control for the assay may also be applied to the support in admixture with a label.

13 Claims, 2 Drawing Sheets

DEPOSITING A BINDER ON A SOLID SUPPORT

This application is a continuation of application Ser. No. 106,075, filed Oct. 8, 1987, now abandoned.

FIELD OF THE INVENTION

This invention relates to a test device useful in an assay for an analyte and to the use thereof in such assays. More particularly, the present invention relates to providing a binder for an analyte on a solid support for use in a solid phase assay for an analyte.

BACKGROUND OF THE INVENTION

Assays for determining analytes by a solid phase technique involve contact between a sample suspected of containing the analyte and a test device having a binder specific for the analyte supported on a solid support. The amount of analyte which becomes bound to the binder on the solid support is then detected with a tracer as a measure (quantitative or qualitative) of analyte in the sample.

In some solid phase assays, for example, as described in U.S. Pat. No. 4,632,901, the binder for the analyte is supported on a limited portion of the solid support in order to provide a test area and an area surrounding the test area which is free of binder. The area free of binder may be employed as a background area to aid in determining of analyte by the use of a suitable tracer. When the test device includes multiple layers, they need to be assembled with the test area oriented correctly relative to the other components of the device. Obtaining proper registry is difficult when the binder is not visible.

SUMMARY OF THE INVENTION

Use of a marker in admixture with a binder allows construction of test devices where a test area of a solid support having binder on it is distinguishable from a background area surrounding the test area. The test device of the present invention is for use in an assay for an analyte. It has a solid support having a test area and a background area. A mixture of binder for the analyte and a marker is supported on the test area. The test kit of the present invention includes the test device and a tracer having a tag which is distinguishable from the marker.

The assay of the present invention employs a test device having a solid support with a test area and a background area. The test device has a mixture of a binder for an analyte and a marker supported on the test area. The test device is contacted with a fluid sample and a tracer. The tracer has a tag which is distinguishable from the marker.

In the manufacturing method of the present invention a solid support which includes a test area and a background area is provided. A mixture of binder and a marker is applied to the test area so that it is supported there. In this manner the marker is useful to determine that binder has in fact been applied to the test areas. The method facilitates assembly of the solid support with other components of the test device without compromising performance of the binder under assay conditions.

The marker which is employed in admixture with the binder is one which does not interfere with the binding properties of the binder, is capable of being supported on the solid support in a manner similar to the binder, and does not interfere with the ability to detect tracer in the test area.

In accordance with a preferred embodiment, the binder is supported on the solid support by adsorption; accordingly, the marker which is employed in admixture with the binder is one which is also capable of being adsorbed by the solid support.

The preferred marker is a material which under appropriate conditions is detectable with the naked eye. The marker may be a colored material which absorbs light of a characteristic band within the visible spectrum. Alternatively, and preferably, the marker is a fluorescent material which upon excitation emits a characteristic fluorescent signal in the visible region of the spectrum. Colored and fluorescent materials are referred to hereafter as "chromogens." With these chromogens, application of the mixture of binder and marker to the test area of the solid support may be easily determined by the presence of color or upon excitation by the presence of a fluorescent signal in the test area.

The marker which is preferably a chromogen, is applied to the solid support in admixture with the binder in an amount which does not adversely affect the binding properties of the binder, and which is sufficient to permit detection of the marker in the test area. The marker is preferably water soluble because in most cases a binder is applied to a solid support in a water based solution.

Thus, by proceeding in accordance with the manufacturing method of the present invention, wherein a binder is applied to the test area of a solid support in admixture with a marker, a test area of the support having binder securely attached it can be distinguished from a background area. In this manner, if the solid support is to be located in a container which includes an inlet port for applying a sample and other materials to the test device, the test area in which the binder is supported can be properly located with respect to the sample inlet port.

In some cases, application of a control (for example an analyte positive control) to a solid support is desirable. In accordance with another aspect of the present invention, the control (in particular a solution containing a known amount of the analyte) is applied to a control area of the solid support in admixture with a label, which is distinguishable from the marker whereby the control area may be determined by detecting the label. In accordance with this aspect of the present invention, the control area may be completely or partially overlapping with the test area or it may be a completely separate area of the support. In most cases, the control is a positive control; however, a negative control may also be applied.

Thus, in accordance with the present invention, the label which is applied to the solid support in admixture with a control is distinguishable from both the tag employed in the tracer used in the assay and from the marker applied in admixture with the binder. The label which is applied in admixture with the control has the characteristics described above with respect to the marker; i.e., the material is one which does not interfere with the binding capabilities of the control, which is capable of being supported by the solid support in a manner similar to the control, which does not interfere with the interactions occurring under assay conditions, and which is distinguishable from the tracer under assay conditions. The label employed in admixture with the control is also preferably a chromogen and most preferably a fluorescent material.

The present invention is useful in any assay where a binder is supported on a solid support. The choice of binder is dependent on the assay format and protocol. The selection of a suitable binder is deemed to be within the scope of those skilled in the art.

The solid support may take a wide variety of forms such as, for example, a sheet or membrane, a test strip, a dip stick, a card, or the like. The selection of a suitable form is deemed to be within the scope of those skilled in the art. Similarly, the solid support may be made of a wider variety of materials. Preferably the support is porous.

DETAILED DESCRIPTION OF THE INVENTION

Figure 1:
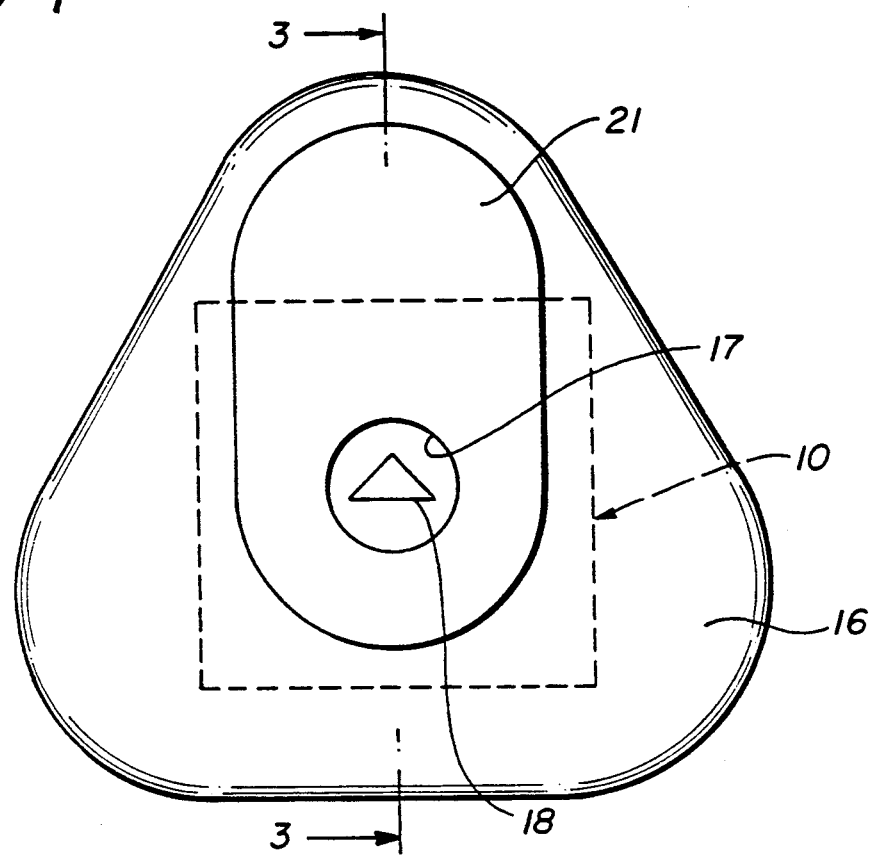
FIG. 1 is a top view of a test device which incorporates the present invention.
Figure 2:
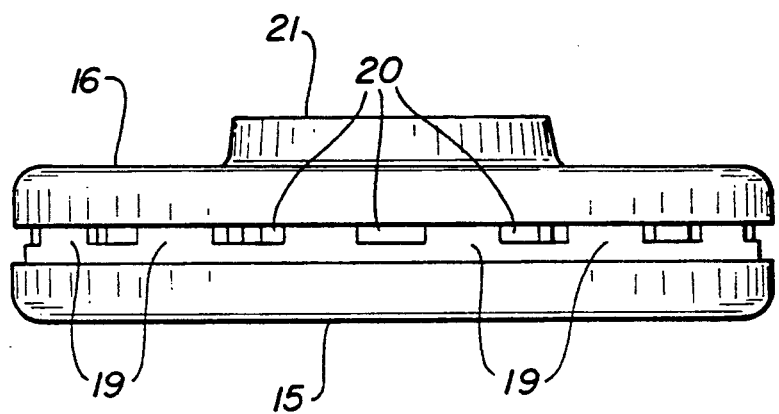
FIG. 2 is a side elevational view of the test device of FIG. 1.
Figure 3:
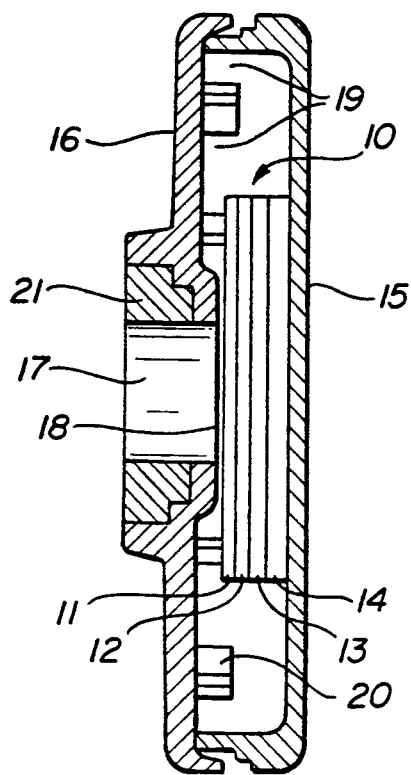
FIG. 3 is a section taken along line 3—3 of FIG. 1.

In accordance with the present invention, a binder which is to be applied to a test area of a solid support, preferably as an aqueous solution or suspension is mixed with a marker, which is preferably a chromogen, and in particular a fluorescent material. The mixture of binder and chromogen is then applied to a defined test area of the solid support, such as, for example, a spot, square, circle, triangle, or any other shape desired, in a manner to support both the binder and the detectable label in the test area. While those skilled in the art are familiar with a variety of coupling techniques to securely attach a binder to a solid support, adsorption is preferred. The procedure for adsorbing the binder can be any of those commonly available for pattern coating of materials including gravure printing, silk screening and other convenional printing methods.

The preferred materials for use as a marker are fluorescent materials which do not adversely affect the binding ability of the binder, and which are capable of being adsorbed by the support. As representative examples of suitable fluorescent materials, there may be mentioned Acridine Orange, Pyronin Y, Texas Red, Rhodamine 6G, with such materials being employed in amounts which do not adversely affect the binding ability of the binder, which are detectable when subjected to ultraviolet light, and which are not detectable with the naked eye. If the material used as a marker includes groups which may be reactive with the binder or control, such groups may be blocked prior to admixing the material, for example they may be placed in a buffer including a source of amino groups (e.g. glycine) that react with reactive sites on the marker and thereby prevent further reactivity which could influence the biological activity of the binder or provide sites for non specific binding under assay conditions.

After the binder has been supported on the solid support, the test area may be distinguished from the background area by detecting the marker. Thus, for example, in the case where the label is a fluorescent material, the support may be exposed to excitation energy of a suitable wave length (e.g. ultraviolet light from conventional U.V. lamps). The marker will emit a characteristic fluorescent signal which is preferably detectable with the naked eye.

In an embodiment employing a control, a solution or suspension of the control and a label which is distinguishable from the marker employed is prepared, with the label preferably being a chromogen, and most preferably a fluorescent material. The solution or suspension of control and label is applied to the solid support in its designated control area, a portion of which or none of which may overlap with the test area. The fact that the control has been applied to the solid support, and the area to which it has been applied, may be determined by detecting the label, for example, in the case of a fluorescent material by exposing the material to excitation energy of a suitable wavelength.

Thus, the binder may be applied to the solid support in admixture with a fluorescent material having a characteristic emission band within the visible spectrum and observable as a first color (such as yellow), and the control may be applied in admixture with a fluorescent material having a characteristic emission band within the visible spectrum and observable as a second color (such as red), which is distinguishable from the first color. After application of both the control and the binder, the solid support may be exposed to excitation energy of suitable wavelengths to detect the presence of both colors to thereby determine the presence, in their respective areas, of both the binder and the control. Preferably the excitation wavelengths for the marker and the label are in the ultraviolet range of the sprectrum and in the absence of U.V. irradiation, they are colorless or are colored with a relatively weak intensity.

The analyte may be determined (qualitatively or quantitatively) by applying a sample suspected of containing the analyte and tracer to the test area. The sample may be applied to an area smaller, equal to or greater than the test area in which the binder is supported. Depending on the chemistry of the assay, reactions take place and presence or absence of a detectable signal from the tracer is indicative of the presence of analyte.

While the chemistry of the assay is independent of the present invention, the preferred assay chemistry uses interactions among specific binding pairs to determine the presence of analyte. The preferred type of specific binding pairs are antigen/antibody pairs.

In the preferred assay chemistry, the tracer is one member of a specific binding pair having a tag coupled to it. For example, if the assay is a competitive format, the specific binding portion of the tracer would be one which is bound by the binder supported on the solid support. If the assay is a sandwich format, then the specific binding portion of the tracer would be bound by the analyte.

Such assay formats and amplification procedures are generally known in the art, and a further description is not required for a complete understanding of the present invention.

The tag portion of the tracer may be any one of a wide variety of materials, including, for example, enzymes, and chromogens. If the tag is detectable by color (as in colormetric enzyme tags and direct detection with a colored material) the color should be observable in the presence of the marker and label. Presently preferred are colored particulate labels, such as liposomes including a chromogen. The selection of a suitable tag is deemed to be within the scope of those skilled in the art.

In the assay technique, the tracer is applied to at least the test area of the solid support, and in the case where a control is used, the tracer is also applied to at least the control area. The tracer may be applied to an area greater than the test area and the control area.

In cases where a positive control is employed, the specific binding portion of the tracer is bound by the positive control whereby the tag of the tracer should be detected in the control area. In addition, if analyte is present in the sample, the tag of the tracer should be detected in the test area.

In accordance with a particularly preferred embodiment of the present invention, the binder in admixture with the marker is supported on a test area located at the surface of a solid support in a concentration whereby a tracer which includes a visible particulate label as its tag portion, under assay conditions, is visible on the support, without further treatment.

The binder supported on the test area is preferably present in at least one microgram per $cm^2$, most generally at least 10 micrograms per $cm^2$, and preferably 40 micrograms per $cm^2$. The residual binding capacity of the test area and the background area may be saturated or blocked by treatment of the solid support with one or more types of proteins which do not specifically bind materials to be employed in the assay. Thus, for example, residual binding capacity may be blocked by use of bovine serum albumin. A wetting agent also may be applied to the test area.

In some cases, in applying the binder (in particular an antibody) to the test area, a polyhydroxy compound (e.g., glycerol, erythritol, and sorbitol), or a sugar (e.g., glucose and sucrose) is included in the antibody solution to prevent non-specific binding (false positives) during the assay.

The solid support which is used is one which has a surface area (area/unit weight of material) such that the binder can be supported on the support in a concentration (weight/unit area) such that the tracer is visible under the assay conditions. The term "visible" as used herein means that the material can be detected with the naked eye without the use of instrumentation; although instrumentation may be used to detect the intensity of the absorbence or fluorescence of the material.

The test area is preferably formed from a cellulose ester with nitrocellulose giving exceptionally good results. The term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Sheets which are formed from cellulose esterified with nitric acid alone, or a mixture of nitric acid and another acid such as acetic acid, are often referred to as nitrocellulose paper.

Although nitrocellulose is a preferred material for the test area (and the entire solid support), other materials having a surface area sufficient for supporting the binder in a concentration as described above may also be employed.

As indicated above, in producing the preferred tracer one member of a specific binding pair is labeled with a particulate label, which is visible. A preferred particulate label is a sac, which includes a color substance whereby the tracer, when used in the assay, is visible without destruction of the sac to release the colored substance.

The sac which is used to label the specific binding portion of the tracer may be any one of a wide variety of sacs, including but not limited to liposomes (single walled or multilamellar) or polymer microcapsules (for example, those made by coaservation, or interfacial polymerization).

Polymer microcapsules also may be produced by procedures known in the art except that the solution in which the microcapsules are formed also includes the tag whereby the interior of the polymer microcapsule includes the tag. The preparation of such microcapsules is disclosed for example in *Microencapsulation Processes and Applications*, edited by Jan E. Vandegger (Plenum Press, 1974). polymer nucleus coated with such a dye or pigment. Such labels are described in more detail in U.S. Pat. No. 4,373,932, which is hereby incorporated by reference. The tracers produced in accordance with that patent may also be employed as tracers in the present invention.

The visible particulate label may be visible polymer particles, such as colored polystryrene particles, preferably of spherical shape.

Representative examples of other suitable particulate labels include ferritin, phycoerythrins or other phycobili-proteins; precipitated or insoluble metals or alloys; fungal, algal, or bacterial pigments or derivatives such as bacterial chlorophylls; plant materials or derivatives, and the like.

The specific binding portion of the tracer may be labeled with the particulate label so as to produce a tracer for use in the invention by procedures generally known in the art, with the procedure which is used being dependent upon the choice of specific binding species and the particulate label. Such techniques include covalent coupling, derivatization or activation, and the like. In producing a tracer wherein the binder is labeled with a sac, the sac may be produced from a component which has been derivatized with a specific binding species, whereby the sac, when produced, is coupled to the specific binding portion.

Thus, the preferred tracer is comprised of a specific binding portion and a particulate label (solid or solid-like, as opposed to non-solid As known in the art, liposomes can be prepared from a wide variety of lipids, including phospholipids, glycolipids, steroids, relatively long chain alkyl esters; e.g., alkyl phosphates, fatty acid esters; e.g., leitchin, fatty amines and the like. A mixture of fatty materials may be employed, such as a combination of neutral steroid, a charged amphiphile and a phospholipid. As illustrative examples of phospholipids, there may be mentioned lecithin, sphingomyelin, dipalmitoyl, and the like. As representative steroids, there may be mentioned cholesterol, cholestanol, lanesterol, and the like. As representative examples of charged amphiphilic compounds, which generally contain from 12 to 30 carbon atoms, there may be mentioned mono- or dialkyl phosphate ester or an alkylamine; e.g., dicetyl phosphate, stearyl amine, hexadecyl amine, dilauryl phosphate, and the like.

The liposome sacs are prepared in an aqueous solution including the tag whereby the sacs will include the tag in their interior. The liposome sacs may be prepared by vigorous agitation in the solution, followed by removal of tag from the exterior of the sac.

Further details with respect to the preparation of liposomes are set forth in U.S. Pat. No. 4,342,826 and PCT International Publication No. WO80/01515, both of which are hereby incorporated by reference.

The tracer may also be produced by labeling the specific binding species with an aqueous dispersion of a hydrophobic dye or pigment, or a labels, such as radioisotopes, enzymes and various fluorescent materials), and the particulate label provides a tag which is visible under the assay conditions so that the presence or amount of analyte may be determined without further treatment and without the use of instrumentation; e.g., by the use of a liposome containing a colored material as the particulate label.

In accordance with a preferred embodiment, the test device is constructed as described in commonly assigned U.S. Ser. No. 016,846, now abandoned and Ser. No. 106,757, filed Aug. 8, 1987. The preferred device includes a porous solid support for supporting the binder at a test area in a concentration whereby the tracer used in the assay, when bound to the test area, under assay conditions is visible without further treatment. It also includes a flow control layer, beneath the porous solid support, which is formed of a porous material having a pore size to control the rate of flow of assay reagents through the test area. The test device also preferably includes a porous spacer layer for spacing an absorbent layer, formed of an absorbent material, from the flow control layer.

The absorbent layer has an absorbency sufficient to absorb the reagent liquids applied to the test layer during the assay. In addition, the absorbent materials functions to provide for flow through the test layer.

The entire porous solid support may be formed of the material used in the test area. Alternatively, only the test area may be formed of such a material.

In addition, since the test device is employed in a manner such that the assay reagents flow through its layers, solid support has a pore size which is greater than the size of the particulate label employed in the assay so that portions of the tracer, which do not become bound under assay conditions, flow into the absorbent layer and are not visible at the test area. In general, the solid support should have a pore size which is at least 2 um, and most preferably at least 5 um. In general, the pore size does not exceed 12 um. It is to be understood, however, that although the previously described pore sizes are preferred, other pore sizes may be employed, depending upon the materials used in the assay.

The flow control layer of the test device is formed of a porous material which is employed to control the rate of flow of assay reagents through the test layer and into the absorbent layer. The preferred porous material which is employed in forming the flow control layer has a pore size which is less than the pore size of the material employed for forming the solid support. Thus, in effect, the flow control layer functions to reduce the rate of flow of assay reagents through the more porous test area.

The pore size of the flow control layer, as well as the thickness of the flow control layer, is preferably controlled in a manner such that the flow of assay reagents through the test area provides the requisite sensitivity as well as a rapid and accurate assay.

In accordance with one particularly preferred embodiment, the layer for controlling rate of flow through the test device is dimensioned and sized in a manner such that the flow rate of materials through the test area is in the order of at least 0.5 ml/min, and generally no more than 2 ml/min.

The flow control layer is preferably formed from a non-fibrous material polycarbonate and having pores or channels of a uniform size that provide for unidirectional flow from the test layer to the layer beneath the flow control layer.

Immediately, below the flow control layer of the preferred test device, a spacer layer is provided. It is a porous material which functions as a spacer between the flow control layer, and the absorbent layer. The porous spacer layer has a pore size greater than the pore size of the flow controlling layer so that the spacer layer does not function to restrict flow through the test device.

The preferred test device also includes an absorbent layer which is a porous material having an absorbing or absorbent capacity sufficient to absorb the liquids which flow into the test device during the assay. The absorbent layer also functions to provide a driving force (e.g., a concentration differential) which causes reagents applied to the test area to flow into the absorbent layer.

Thus, in accordance with the preferred embodiment of the present invention, an assay employs a tracer wherein the tag portion of the tracer is a visible particulate sac, and wherein the assay is performed on a test device, which is preferably formed from a plurality of layers of material having different characteristics, as described above, and wherein the assay reagents flow through the test area of the test device.

The materials which are employed in forming the various layers of the test device are selected to have the characteristics described above. In addition, such materials should not produce non-specific binding of analyte or tracer. The materials may inherently have such characteristics, or alternatively, the materials may be treated to prevent nonspecific binding; for example, treatment with an appropriate protein, such as bovine serum albumin. The solid support of the test device is preferably also treated with a wetting agent in order to insure proper flow of the assay reagents through the test layer and into the absorbent layer. Representative examples of wetting agents include sucrose, glycerol, glucose, and sorbitol. The solid support may be simultaneously treated with a protein and wetting agent; e.g., an aqueous solution of bovine serum albumin and sucrose.

In general, the test device is mounted on or in a suitable holder, such as a card or a container. The selection of a suitable holder for the test device is deemed to be within the scope of those skilled in the art.

In addition, the preferred test device is provided with a cover having an aperature, which directs assay reagents to the test area. Thus, for example, the test device may be covered with a card including an aperture which overlies the test area whereby the liquid sample and various assay reagents are applied directly to the test area. Alternatively, the test device may be placed in a container which includes a suitable aperture for directing the sample and assay reagents to the test area. The use of a marker in admixture with the binder identifies the test area whereby it may be properly positioned with respect to the aperture.

Referring now to the drawings, a test device, generally designated as 10, comprised of a solid support, generally designated as 11, which has a test area for supporting a binder. A preferred material is nitrocellulose, which has a pore size in excess of 2 microns, and generally less than 12 microns. Most preferred is a pore size of about 5 microns.

Immediately underneath the layer 11 is a flow control layer 12 which is preferably formed from a unidirectional flow controlling polycarbonate membrane having a pore size of 0.6 microns.

Immediately underneath flow controlling layer 12 a spacer layer 13 is provided. The spacer layer 13 is formed of a porous material, and generally has a pore size greater than the pore size of flow controlling layer 12. The layer 13 may be formed, for example, from a non-woven polyacetate.

Immediately underneath spacer layer 13 and in contact therewith is absorbent layer 14. The absorbent layer 14 is preferably formed from a cellulose material, e.g., absorbent cellulose paper.

Thus, the test device is comprised of layers 11, 12, 13 and 14, which are preferably combined to produce a unified device 10. The layers may be attached to each other, for example, by sewing of the layers to each other; however, other methods of attachment are possible.

As particularly shown, the test device 10 is in a test container which includes a base 15, and a cover 16. The base 15 has a depth such that the device 10 is within the container. In the preferred embodiment the container has three sides in a generally triangular shape with rounded corners.

The cover 16 includes a raised portion having a suitable aperture 17 which overlies the test area 18 of the solid support 11. Preferably, a portion of the background area of the support 11 surrounding the test area is also within the opening defined by aperature 17.

The cover 16 is supported over layer 11 by projections 19 extending upward from the sides of the base 15. The projections 19 are of sufficient height so as to provide air spaces 20 which provide for ventilation of the sides of the device 10. The air spaces 20 are bounded by the projections 19, the cover 16, and the base 15.

The raised portion of the cover 16 surrounding the aperture 17 include a colored area 21, the color of which preferably contrasts from that of the cover 16 and the color to be generated in test area 18 to provide for a better reading of the test results which are generally determined by color. In the preferred embodiment, base 15, cover 16, and colored area 21 are made of plastic materials.

For use of the test device 10 in a sandwich fluorescent signal when exposed to ultraviolet energy.

In manufacturing the test article, solid support 11 is initially treated with a mixture of binder and marker which may be a first fluorescent material to apply the mixture to test area 101. Thereafter, a mixture of the control and label which may be a second fluorescent material is applied to the control area 102. As shown, control area 102 is smaller and lies within area 101.

The fact that the analyte and binder have been deposited in their respective areas may then be determined by exposing solid support 11 to ultraviolet light and determining the presence of the respective fluorescent emission colors in the appropriate areas.

Thereafter, solid support 11 may be combined with the other layers, and the device 10 positioned in the test container in a manner such that the test area 101 is beneath aperture 17, whereby assay reagents may be directed to the area in which the binder and control is supported.

Figure 4A:
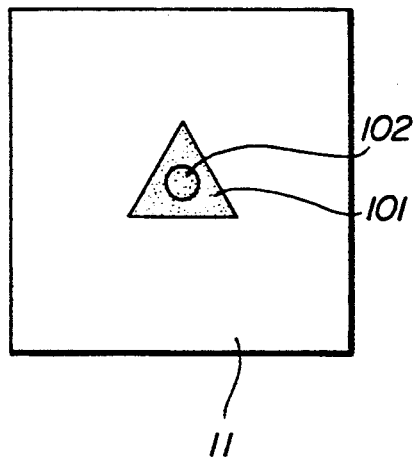
FIGS. 4A and 4B are simplified schematic representations of alternative versions of first layer 11 which includes a binder and control.
Figure 4B:
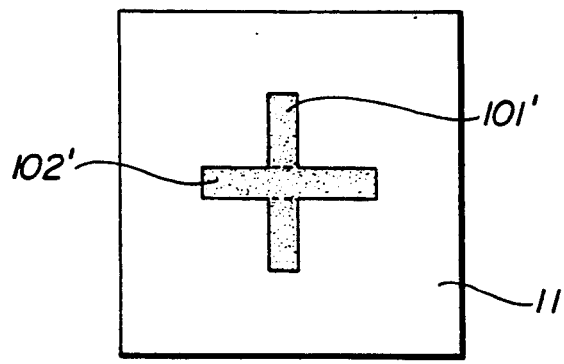

An alternative embodiment is shown in FIG. 4B wherein control area 102' is where the control is deposited and test area 101' is where the binder is deposited. As should be apparent, the presence of the control and the binder in their respective areas may be determined as described with reference to FIG. 4A.

In the embodiment of FIG. 4B, if no analyte is present, only area 102' is colored by the tracer, thereby indicating a negative sign on the layer 11. If analyte is present in the sample, assay, the binder may be an antibody specific for the analyte to be determined. If the sandwich assay is to be operated in a sequential mode a sample which is suspected of containing the analyte is applied to the test area through the aperture 17 whereby the sample contacts the binder in test area 18, with the sample flowing through the test device to the absorbent layer 14. The analyte present in the sample will become specifically bound to the binder in area 18.

Thereafter, tracer is applied to the test device through the aperture 17. The tracer becomes bound to the analyte, and any unbound portion flows through the test device to the absorbent layer 14.

If desired, a wash solution may be applied to the test device 10 prior to addition of the tracer. Similarly, after addition of the tracer, a wash solution may be applied to the test device to wash any tracer which may not be specifically bound to the complex in area 18, into the absorbent layer 14.

The presence of color in area 18 is indicative of the presence of analyte, and if the assay is to be a quantitative assay, the intensity of such color is indicative of the quantity of analyte present in the sample.

Referring now to FIG. 4A solid substrate 11 includes a test area 101 and control area 102. Test area 101 includes a mixture of the binder used in the assay and a marker, such as a fluorescent material. Control area 102 includes an analyte control in admixture with a label, preferably a second fluorescent material, which emits a both areas 101' and 102' will be colored, whereby a plus sign is displayed, indicating the presence of analyte in the sample.

Although the invention has been described with respect to a preferred embodiment as shown in the drawings, the present invention is equally applicable to depositing binder, and optionally also control on a solid support other than one particularly shown. Thus, for example, the test device may be in the form of a single layer, or two layers. Similarly, the test layer may be other than a membrane as shown.

These and other modifications should be apparent to those skilled in the art.

EXAMPLE

A sulfonyl chloride derivative of sulforhodamine 101 (available from Molecular Probes Cat. T353 as Texas Red Dye), after having been incubated for two hours in a 0.1 M glycine buffer pH 8.0 is combined with rabbit anti-group A Streptococcus antibody (n-acetyl glucosamine affinity purified) in a concentration ranging from 0.5 to 20 ug/ml. Separately Group A Streptococcus antigen is extracted with nitrous acid (300 ul HCl (0.1 M) with 40 ul $NaNO_2$ (4M) and after three minutes 40 ul Tris buffer (1M, Trizma ™ base (Sigma), with 4M NaCl)is added). To the extracted antigen is added Rhodamine 6G dye (Allied Cat. 663) in glycine buffer (0.1M) pH 8.0 to provide a concentration of less than 4 ug/ml.

Each of the above solutions is applied to nitrocellulose membrane (Schleicher & Schuell, pore size 5 microns) and under long wave (290-350 nm) ultraviolet excitation, the Texas Red, which fluoresces red, may be distinguished from the Rhodamine 6G which fluoresces bright yellow. The presence of the two colors discriminates and identifies the location of the antibody binder and antigen positive control.

The nitrocellulose containing the mixture of antibody and fluorescent material as well as the mixture of antigen positive control and fluorescent material is used in a sandwich assay for detecting Group A Strep antigen in which the tracer is affinity purified antibody (rabbit anti-group A Strep) covalently coupled to liposomes containing sulfo-rhodamine B dye (the procedure for making this tracer is described in South Africa Patent No. 84/9397 corresponding to allowed U.S. Ser. No. 579,667 which is hereby incorporated by reference).

The presence of the fluorescent material with the antibody binder and with the antigen positive control on the nitrocellulose support does not adversely affect sensitivity at $5 \times 10^5$ organisms/ml.

The present invention is applicable to procedures and products for determining a wide variety of analytes. As representative examples of types of analytes, there may be mentioned; drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; and products or components of normal or malignant cells. As particular examples, there may be mentioned $T_4$; $T_3$; digoxin; hCG; insulin; theophylline; luteinizing hormone; organisms causing or associated with various disease states, such as *Streptococcus Pyogenes* (group A), Herpes Simplex I and II, cytomegalovirus, rubella, chlamydia, and *Candida Albicans*.

The analyte may be determined in various samples, including, for example, body fluids, such as saliva, urine, serum, and cerebral spinal fluid or from swab samples, e.g., from the throat.

Numerous modifications and variations of the present invention are possible in light of the above, and therefore, within the scope of the appended claims, the invention may be practiced otherwise than as particularly described.

What is claimed is:

1. A test device for use in detecting the presence of an analyte, comprising:
   a casing having an aperture;
   a solid support comprising an upper surface and contained in said casing;
   a test area on the upper surface of said support and positioned in registry with said aperture;
   a binder for said analyte attached to said test area;
   a detectable chromogen marker attached to said binder, related to the presence or absence of the binder which does not interfere with said assay; and
   a background area on the upper surface of said support without binder and detectable marker;
   wherein:
   said marker causes the binder to be distinguishable from said support so that, before the device is used in said assay the device is examined to confirm that binder is present in said test area.

2. A test device for use in an assay for detecting the presence of an analyte, comprising:
   a solid support comprising an upper surface and a lower surface;
   a test area on the upper surface of said support;
   a binder for the analyte attached to said test area;
   a detectable marker attached to said binder which is related to the presence or absence of the binder, and does not interfere with said assay; and
   a background area on the upper surface of said support without binder and detectable marker;
   a control area on the upper surface of said support;
   an assay control attached to said control area; and
   a detectable label attached to said assay control which is distinguishable and does not interfere with the assay or with the detectable marker;
   wherein:
   the detectable marker causes the binder to be distinguishable from said support so that, before the device is used in said assay the device is examined to confirm that binder is present in said test area; and
   said label causes the assay control to be distinguishable from said support so that before the device is used in said assay the device is examined to confirm that assay control is present on said support.

3. The test device of claim 2 wherein the assay control is a positive analyte control.

4. The test device of claim 3 wherein said control area is attached to said test area.

5. The test device of claim 2 wherein the label is a chromogen.

6. The test device of claim 5 wherein the solid support is nitrocellulose.

7. A process for producing a test device suitable for detecting the presence of an analyte, comprising:
   providing a solid support comprising an upper surface;
   contacting said upper surface with a binder for said analyte;
   contacting said binder with a detectable marker related to the presence or absence of the binder which does not interfere with said assay;
   detecting the marker to confirm that binder is present in said device; and
   placing the support in a casing including an aperture with the test area in registry with the aperture.

8. The process of claim 7 further comprising:
   contacting said upper surface with a mixture of an assay control; and
   contacting said assay control with a detectable label;
   wherein:
   said control area is distinguishable from said test area and said support, and said label is related to the presence or absence of said assay control.

9. The process of claim 8 wherein said control area is attached to said test area.

10. The process of claim 8 wherein the marker is a fluorescent material and the label is a different fluorescent material.

11. The process of claim 7 wherein the marker is a chromogen.

12. The process of claim 7 wherein the marker is a fluorescent dye.

13. The process of claim 7 wherein the support is nitrocellulose.

* * * * *

UNITED STATES PATENT AND TRADEMARK OFFICE
CERTIFICATE OF CORRECTION

PATENT NO. : 5,073,340

DATED : December 17, 1991

INVENTOR(S) : Covington et al.

Page 1 of 4

It is certified that error appears in the above-identified patent and that said Letters Patent is hereby corrected as shown below:

At Claim 1, column 11, line 57, "marker attached to said binder" should be replaced with -- marker attached with said binder --.

At Claim 2, column 12, line 7, "marker attached to said binder" should be replaced with -- marker attached with said binder --.

UNITED STATES PATENT AND TRADEMARK OFFICE
CERTIFICATE OF CORRECTION

PATENT NO. : 5,073,340

DATED : December 17, 1991

INVENTOR(S) : Covington et al

It is certified that error appears in the above-indentified patent and that said Letters Patent is hereby corrected as shown below:

-- As known in the art, liposomes can be prepared from a wide variety of lipids, including phospholipids, glycolipids, steroids, relatively long chain alkyl esters; e.g., alkyl phosphates, fatty acid esters; e.g., leitchin, fatty amines and the like. A mixture of fatty materials may be employed, such as a combination of neutral steroid, a charged amphiphile and a phospholipid. As illustrative examples of phospholipids, there may be mentioned lecithin, sphingomyelin, dipalmitoyl, and the like. As representative steroids, there may be mentioned cholesterol, cholestanol, lanesterol, and the like. As representative examples of charged amphiphilic compounds, which generally contain from 12 to 30 carbon atoms, there may be mentioned mono- or dialkyl phosphate ester or an alkylamine; e.g. dicetyl phosphate, stearyl amine, hexadecyl amine, dilauryl phosphate, and the like.

The liposome sacs are prepared in an aqueous solution including the tag whereby the sacs will include the tag in their interior. The liposome sacs may be prepared by vigorous agitation in the solution, followed by removal of tag from the exterior of the sac.

Further details with respect to the preparation of liposomes are set forth in U.S. Patent No. 4,342,826 and PCT International Publication No. WO80/01515, both of which are hereby incorporated by reference.

The tracer may also be produced by labeling the specific binding species with an aqueous dispersion of a hydrophobic dye or pigment, or a --

At column 6, lines 47-68, after "non-solid" and at column 7, lines 1-7 before "or a labels," delete the text therein included.

UNITED STATES PATENT AND TRADEMARK OFFICE
CERTIFICATE OF CORRECTION

PATENT NO. : 5,073,340
DATED : December 17, 1991
INVENTOR(S) : Covington, et al

It is certified that error appears in the above-indentified patent and that said Letters Patent is hereby corrected as shown below:

-- assay, the binder may be an antibody specific for the analyte to be determined. If the sandwich assay is to be operated in a sequential mode a sample which is suspected of containing the analyte is applied to the test area through the aperture 17 whereby the sample contacts the binder in test area 18, with the sample flowing through the test device to the absorbent layer 14. The analyte present in the sample will become specifically bound to the binder in area 18.

Thereafter, tracer is applied to the test device through the aperture 17. The tracer becomes bound to the analyte, and any unbound portion flows through the test device to the absorbent layer 14.

If desired, a wash solution may be applied to the test device 10 prior to addition of the tracer. Similarly, after addition of the tracer, a wash solution may be applied to the test device to wash any tracer which may not be specifically bound to the complex in area 18, into the absorbent layer 14.

UNITED STATES PATENT AND TRADEMARK OFFICE
CERTIFICATE OF CORRECTION

PATENT NO. : 5,073,340

DATED : December 17, 1991

INVENTOR(S) : Covington, et al

It is certified that error appears in the above-indentified patent and that said Letters Patent is hereby corrected as shown below:

The presence of color in area 18 is indicative of the presence of analyte, and if the assay is to be a quantitative assay, the intensity of such color is indicative of the quantity of analyte present in the sample.
 Referring now to Figure 4A solid substrate 11 includes a test area 101 and control area 102. Test area 101 includes a mixture of the binder used in the assay and a marker, such as a fluorescent material. Control area 102 includes an analyte control in admixture with a label, preferably a second fluorescent material, which emits a --

At column 10, lines 10-38, after "sample" and before "both areas", delete the text therein included.

Signed and Sealed this

Twenty-fourth Day of May, 1994

Attest:

BRUCE LEHMAN

*Attesting Officer*        *Commissioner of Patents and Trademarks*